United States Patent [19]

Greiner et al.

[11] Patent Number: 5,629,330
[45] Date of Patent: *May 13, 1997

[54] FUNGICIDAL COMPOSITION FOR SEED DRESSING

[75] Inventors: Alfred Greiner, St Cyr au Mont d'or; Jean Hutt, Lyons; Jacques Mugnier, La Balme, de Sillingy; Regis Pepin, Rilleux la Pape, all of France

[73] Assignee: Rhone Poulenc Secteur Agrochimie, Lyons, France

[*] Notice: The term of this patent shall not extend beyond the expiration date of Pat. No. 5,256,683.

[21] Appl. No.: 162,494

[22] Filed: Dec. 3, 1993

Related U.S. Application Data

[62] Division of Ser. No. 714,726, Jun. 13, 1991, Pat. No. 5,290,791.

[30] Foreign Application Priority Data

Mar. 5, 1991 [FR] France .................. 9007607

[51] Int. Cl.$^6$ .............. A01N 43/76; A01N 43/653; A01N 43/50; A01N 43/38
[52] U.S. Cl. .............. 514/376; 514/383; 514/391; 514/421; 504/100
[58] Field of Search .................. 514/383, 391, 514/376, 421; 504/100

[56] References Cited

U.S. PATENT DOCUMENTS 3,823,240  7/1974  Sauli ............... 514/391
5,256,683  10/1993  Hutt et al. .............. 514/383
5,455,261  10/1995  Greiner et al. .......... 514/383

FOREIGN PATENT DOCUMENTS 378953  12/1989  France.

OTHER PUBLICATIONS

Farm Chemicals Handbook '87, Meister Publishing Co., Ohio, 1987, pp. C143–C144.
Fine Chemicals Directory Search System entry for 2,2-dimethylcyclopentanone (1994).
Worthing et al., The Pesticide Manual, 8th Ed., British Crop Protection Council, pp. 371, 451–452 (1987).
Cameron et al., Chemical Abstracts vol. 106, 104: 207445k (1986).

*Primary Examiner*—John Pak
*Attorney, Agent, or Firm*—Morgan & Finnegan, L.L.P.

[57] ABSTRACT

The present invention relates to a fungicidal composition intended for the protection of the multiplication products of cultivated plants, containing:

(a) 2-(4-chlorobenzylidene)-5,5-dimethyl-1-(1H-1,2,4-triazol-1-ylmethyl)-1-cyclopentanol;

(b) one or more fungicides suitable for the protection of the said multiplication products, optionally one or more insecticides, (c), an agriculturally acceptable inert vehicle and an agriculturally acceptable surfactant.

The invention also relates to a method for protecting the multiplication products of plants against fungal diseases using these compositions.

4 Claims, No Drawings

FUNGICIDAL COMPOSITION FOR SEED DRESSING

This is a divisional of application Ser. No. 07/714,726 filed Jun. 13, 1991, which is U.S. Pat. No. 5,290,791.

CLAIM OF PRIORITY

This application claims the benefit of the following prior application: French Ser. No. 9007607 filed on Jun. 13, 1990.

The present invention relates to a fungicidal composition intended, in particular, for the protection of the multiplication products of cultivated plants, containing (a) 2-(4-chlorobenzylidene)-5,5-dimethyl-1-(1H-1,2,4-triazol-1-ylmethyl)-1-cyclopentanol, (b) one or more fungicides suitable for the protection of the said multiplication products, an agriculturally acceptable inert vehicle and optionally an agriculturally acceptable surfactant.

The invention also relates to a process for protecting the multiplication products and the plants resulting therefrom against fungal diseases using a composition according to the invention. It also relates to the said multiplication products coated with the said composition.

2-(4-chlorobenzylidene)-5,5-dimethyl-1-(1H-1,2,4-triazol-1-ylmethyl)-1-cyclopentanol is described in European Patent Application No. 89/420,520 filed on 27th Dec. 1989 and not published to date.

The compound 2-(4-chlorobenzylidene)-5,5-dimethyl-1-(1H-1,2,4-triazol-1-ylmethyl)-1-cyclopentanol may be obtained in the following manner:

10% aqueous sodium hydroxide solution (100 ml) is added to a mixture of 2,2-dimethylcyclopentanone (10 g) and 4-chlorobenzaldehyde (13.8 g) in ethanol (100 ml) at 0° C. After 30 minutes, a thick slurry is filtered and the solid is washed and then dried. 2,2-Dimethyl-5-(4-chlorobenzylidene)-1-cyclopentanone (12.5 g), m.p. 120° C., is obtained. This compound, dissolved in THF (50 ml), is added to a solution formed in the following manner: sodium hydride (80% dispersion in mineral oil) (1.9 g) in anhydrous DMSO (50 ml) is heated to 80° C. until the solid has dissolved completely. The solution is then diluted with THF (100 ml) and then cooled to −10° C. A solution of trimethylsulphonium iodide (11.5 g) in dimethyl sulphoxide (80 ml) is added to the mixture in the course of 10 minutes and the mixture is stirred for 15 minutes at −10° C. A solution of 2,2-dimethyl-4-chloro-5-(4-chlorobenzylidene)-1-cyclopentanone (11.8 g) in THF (100 ml) is then added.

The mixture thereby produced is left at room temperature, then poured into water and extracted with ether, and the organic phase is washed with water, dried and distilled. 7-(4-Chlorobenzylidene)-4,4-dimethyl-1-oxaspiro[2.4] heptane is obtained, which product is used directly for the next step.

A mixture of the product (5 g) with 1,2,4-triazole (2.8 g) and potassium carbonate (11 g) is heated in N,N-dimethylformamide (40 ml) for 4 hours. The mixture is poured into water and extracted with ethyl acetate. The organic phase is washed and dried and the product is recrystallised to obtain the stated compound, m.p. 143° C.

The chemical structure of the fungicide (a) or 2-(4-chlorobenzylidene)-5,5-dimethyl-1-(1H-1,2,4-triazol-1-ylmethyl)-1-cyclopentanol is given below.

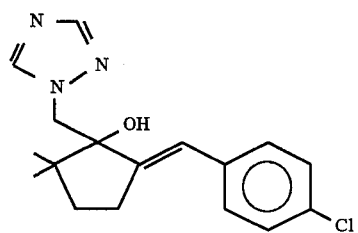

The structure of the composition is very predominantly (>95%) that in which the para-chlorophenyl group is in the E position relative to the carbon bearing the hydroxyl group.

2,2-Dimethylcyclopentanone may be obtained in a manner known from the literature, or is available on the market (see Fine Chemical Directory).

The term "multiplication product" is understood to denote al the generative parts of the plant which can be used for the multiplication of the latter. There may be mentioned, e.g., the seeds (in the strict sense), roots, fruits, tubers, bulbs, rhizomes, parts of plants. Germinated plants and young plants which are to be transplanted after germination or after emergence from the soil, may also be mentioned. These young plants may be protected before transplantation by a total or partial treatment by immersion.

To choose the fungicides suitable for the protection of the multiplication products, those skilled in the art may usefully refer to the information given in the reference works and which mention the absence of phytotoxicity of the said products.

Among these works, the plant-protection index, 1990 edition, ACTA 75595 PARIS CEDEX 12., may be mentioned.

The compositions according to the invention usually contain between 0.5 and 95% of active substances.

The term "vehicle" in the present description denotes a natural or synthetic, organic or inorganic material with which the active substance is combined in order to facilitate its application to the plant, to the seeds or to the soil. This vehicle is hence generally inert, and it must be agriculturally acceptable, in particular to the plant being treated. The vehicle may be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquefied gases, and the like).

The surfactant can be an emulsifying, dispersing or wetting agent of the ionic or nonionic type. There may be mentioned, e.g., polyacrylic acid salts, lignosulphonic acid salts, phenolsuphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyltaurides) and polycondensates of ethylene oxide with phosphoric esters of alcohols or phenols. The presence of at least one surfactant is often required because the active substance and/or the inert vehicle are not soluble in water and the carrier agent for the application is water.

These compositions can also contain any other kind of ingredient, such as, e.g., protective colloids, adhesives, thickeners, thixotropic agents, penetrating agents, stabilizers, sequestering agents, pigments, colorings and polymers.

More generally, the compositions according to the invention may be combined with all solid or liquid additives corresponding to the usual techniques of formulation for application to seed dressing, in particular.

It will be noted, in this connection, that, in the jargon of those skilled in the art, the term seed dressing refers, in fact, to treatment of the fertilized and ripened ovule.

The techniques of application are well known to those skilled in the art, and they may be used readily in the context of the present invention.

There may be mentioned, e.g., film-coating or encapsulation.

Among compositions, solid or liquid compositions may, generally speaking, be mentioned.

As solid forms of compositions, there may be mentioned powders for dusting or dispersing (having a content of compound of formula (I) which can range up to 100%) and granules, in particular those obtained by extrusion, by compaction, by impregnation of a granular vehicle or by granulation from a powder (the content of compound of formula (I) in these granules being between 1 and 80% for these latter cases).

The composition may also be used in the form of a dusting powder; a composition comprising active substance (50 g), finely divided silica (10 g), organic pigment (10 g) and talc (970 g) may thus be used; these constituents are mixed and ground and the mixture is applied by dusting.

As liquid forms of compositions, or forms intended for making liquid compositions when they are applied, there may be mentioned solutions, especially water-soluble concentrates, emulsifiable concentrates, emulsions, flowables, aerosols, wettable powders (or powder for spraying), pastes and dispersible granules.

The emulsifiable or soluble concentrates most often comprise 10 to 80% of active substance, the emulsions or solutions ready for application containing for their part 0.01 to 20% of active substance.

For example, in addition to the solvent, the emulsifiable concentrates can contain, when necessary, 2 to 20% of suitable additives such as the stabilizers, surfactants, penetrating agents, corrosion inhibitors, coloring or adhesives mentioned above.

From these concentrates, emulsions of any desired concentration, which are especially suitable for application to seeds, may be obtained by dilution with water.

The flowables, also applicable by spraying, are prepared so as to obtain a stable fluid product which does not settle out, and they usually contain from 10 to 75% of active substance, from 0.5 to 15% of surfactants, from 0.1 to 10% of thixotropic agents, from 0 to 10% of suitable additives such as pigments, colorings, antifoams, corrosion inhibitors, stabilizers, penetrating agents and adhesives, and, as a vehicle, water or an organic liquid in which the active substance is soluble to only a slight extent if at all: some solid organic substances or inorganic salts may be dissolved in the vehicle to assist in preventing sedimentation or as antifreezes for the water.

The wettable powders (or powder for spraying) are usually prepared so that they contain 20 to 95% of active substance, and they usually contain, in addition to the solid vehicle, from 0 to 5% of a wetting agent, from 3 to 10% of a dispersant agent and, when necessary, from 0 to 10% of one or more stabilizers and/or other additives such as pigments, colorings, penetrating agents, adhesives or anticaking agents, and the like.

To obtain these powders for spraying or wettable powders, the active substances are mixed intimately in suitable blenders with the additional substances and the mixture is ground using mills or other suitable grinders. Powders for spraying are thereby obtained, the wettability and suspendibility of which are advantageous; they may be suspended in water at any desired concentration, and these suspensions are very advantageously usable, especially for application to seeds.

In place of wettable powders, pastes may be made. The conditions and procedures for making and using these pastes are similar to those for the wettable powders or powders for spraying.

The dispersible granules are usually prepared by agglomeration, in suitable granulation systems, of compositions of the wettable powder type.

As already stated, the aqueous dispersions and emulsions, e.g., the compositions obtained by diluting a wettable powder or an emulsifiable concentrate according to the invention with water, are included in the general scope of the present invention. The emulsions can be of the water-in-oil or oil-in-water type, and they can have a thick consistency such as that of a "mayonnaise".

Among these compositions, those skilled in the art will advantageously choose that or those which are suitable according to the chosen combinations.

According to a preferred variant, a feature of the composition according to the invention is that the weight ratio of the fungicide a) 2-(4-chlorobenzylidene)-5,5-dimethyl-1-(1H-1,2,4-triazol-1-ylmethyl)-1-cyclopentanol to the fungicide(s) b) is between 1/400 and 400.

From an industrial standpoint, the multiplication product is preferably a seed for cereals, maize, rape, sunflower, soybean, alfalfa and rice. For potatoes, it can advantageously be a tuber.

Compositions can be binary, ternary or quaternary according to the use for which they are intended.

According to a first preferred variant, the fungicide b) is a broad-spectrum fungicide chosen from dithiocarbamic acid derivatives, of which the following (according to the common name agreed by the British Standard Institution or BSI or the IUPAC name) may be mentioned:

ferbam or iron tris(dimethyldithiocarbamate),
ziram or zinc bis(dimethyldithiocarbamate),
nabam or disodium ethylenebis(dithiocarbamate),
zineb or zinc ethylenebis(dithiocarbamate) (polymer),
maneb or manganese ethylenebis(dithiocarbamate) (polymer),
mancopper,
mancozeb or complex of manganese ethylenebis (dithiocarbamate) (polymer) with a zinc salt,
propineb or polymeric zinc propylenebis (dithiocarbamate),
metam-sodium,
cuprobam,
thiram or tetramethylthiuram disulphide or TMTD,
carbatene or metiram, or from dicarboximide derivatives, of which the following may be mentioned:

captan or N-(trichloromethylthio)cyclohex-4-ene-1,2-dicarboximide,
folpel or N-(trichloromethylthio)phthalimide,
captafol or N-(1,1,2,2-tetrachloroethylthio)cyclohex-4-ene-1,2-dicarboximide,
ditalimfos, iprodione or 3-(3,5-dichlorophenyl)-N-isopropyl-2,4-dioxoimidazolidine-1-carboxamide, procymidone or N-(3,5-dichlorophenyl)-1,2-dimethylcyclopropane-1,2-dicarboximide, vinclozolin or (RS)-3-(3,5-dichlorophenyl)-5-methyl-5-vinyl-1,3-oxazolidine-2,4-dione.

Among these derivatives, the following broad-spectrum fungicides are preferred: captan, thiram, maneb.

According to a second preferred variant, optionally taken in combination with the first variant when the fungicide b) is a mixture, the fungicide b) is a fungicide having anti-Fusarium activity, preferably chosen from imidazoles, of which the following may be mentioned:

prochloraz or N-propyl-N-[2-(2,4,6-trichlorophenoxy) ethyl]imidazole-1-carboxamide, imazalil or allyl 1-(2,4-dichlorophenyl)-2-imidazol-1-ylethyl ether, or from carbomates, of which the following may be mentioned:

benomyl or methyl 1-(butylcarbamoyl)benzimidazol-2-ylcarbamate, thiabendazole or 2-(thiazol-4-yl)benzimidazole, carbendaim or methyl benzimidazol-2-ylcarbamate, or from pyrroles, of which the following may be mentioned:

fenpiclonil or 4-(2,3-dichlorophenyl)pyrrole-3-carbonitrile or alternatively oxine-copper.

According to a third preferred variant, optimally taken in combination with one of the first two variants or both when b) is a mixture, the fungicide b) is fungicide having anti-Rhizoctonia activity, preferably chosen from dicarboximides, of which the following may be mentioned:

iprodione, phenylureas, of which the following may be mentioned:

pencycuron or 1-(4-chlorobenzyl)-1-cyclopentyl-3-phenylurea, or anilides, of which the following may be mentioned:

mepronil flutolanil or α,α,α-trifluoro-3'-isopropoy-o-toluanilide, or phosphorus derivatives such as tolclofos-methyl or 0-2,6-dichloro-p-tolyl, O,O-dimethyl phosphorothioate.

According to a fourth preferred variant, taken or otherwise in combination with one or two of the first three, or all three, the fungicide b) is a fungicide having anti-Oomycetes activity, preferably chosen from acylalanines:

benalaxyl or methyl N-phenylacetyl-N-(2-6-xylyl)-DL-alaninate, furalaxyl or methyl N-(2-furoyl)-N-(2,6-xylyl)-DL-alaninate, metalaxyl or methyl N-(2-methoxyacetyl)-N-(2,6-xylyl)-DL-alaninate, oxadixyl or 2-methoxy-N-(2-oxo-1,3-oxazolidin-3-yl) acet-2',6'-xylidide thiadiazoles, of which the following may be mentioned:

etridiazole or ethyl 3-trichloromethyl-1,2,4-thiadiazol-5-yl ether isoxazoles, of which the following may be mentioned:

hymexazol or 5-methylisoxazol-3-ol, metal monoethyl phosphites, of which the following may be mentioned:

fosetyl-Al or aluminum ethyl hydrogen phosphonate, phosphorous acid or its alkali metal (for example sodium or potassium) or alkaline earth metal (for example calcium) salts.

According to a fifth preferred variant, taken or otherwise in combination with one or two or three of the first four, or all four, the fungicide b) is a fungicide having anti-Oidium activity, preferably chosen from: morpholines at a non-phytotoxic dose:

fenpropidin or (RS)-1-[3-(4-tert-butylphenyl)-2-methylpropyl]piperidine, fenpropimorph or (±)-cis-4-[3-(4-tert-butylphenyl)-2-methylpropyl]-2,6-dimethylmorpholine, tridemorph or 2,6-dimethyl-4-t4idecylmorpholine, 4-[3-(4-chlorophenoxyphenyl)-2-methylpropyl]-2,6-dimethylmorpholine described in EP-A-262,870 of 24th Sep. 1987;

pyrimidines such as:

ethirimol or 5-butyl-2-ethylamino-6-methylpyrimidin-4-ol.

According to a sixth variant, taken or otherwise in combination with one or more of the first five, the fungicide b) is a fungicide having anti-Helminthosporium or anti-caries, anti-smut or anti-septorioses activity, preferably chosen from:

triazoxide, fenfuram or 2-methyl-3-furanilide, carboxin or 5,6-dihydro-2-methyl-1,4-oxathiine-3-carboxanilide, guazatine, iminoctadine dodecylbenzenesulphonate, ampropylfos or 1-aminopropylphosphonic acid.

The subject of the invention is also a fungicidal composition as described above containing, in addition, one or more insecticides c) which are suitable for the protection of the multiplication products.

Among the latter, the following may be mentioned: tefluthrin, cypermethrin, thiodicarb, lindane, furathiocarb, acephate, butocarboxim, carbofuran, NTN, endosulfan, diethion, aldoxycarb, methiocarb, oftanol, (isofenphos), chlorpyrifos, bendiocarb, benfuracarb, oxamyl, parathion, capfos, dimethoate, fonofos, chlorfenvinphos, cartap, fenthion, fenitrothion, HCH, deltamethrin, malathion, diazinon, disulfoton.

The compositions according to the invention may be used for both the preventive and the curative protection of the multiplication products of plants against fungi, in particular of the basidiomycete, ascomycete, adelomycete or Fungi imperfecti type, especially rusts, smuts, oidia, eyespote, fusarioses, Fusarium roseu, Fusarium nivale, helminthosporioses, rhynchosporioses, septorioses and rhizoctonia disease of vegetable organisms and plants in general, and especially of cereals such as wheat, barley, rye, oats and hybrids thereof, and also rice and maize.

The compositions according to the invention are especially active against fungi, in particular of the basidiomycete, ascomycete, adelomycete or Fungi Imperfecti type, such as *Botrytis cinerea, Erysiphe graminis, Puccinia graminis, Puccinia recondita, Piricularia oryzae, Cercospora beticola, Puccinia striiformis, Erysiphe cichoracearum, Rhinchosporium secalis*, Fusarium, Solani, *Fusarium oxysporum* (e.g. *melonis*), *Pyrenophora avenae, Septoria tritici, Septoria avenae, Whetzelinia sclerotiorum, Mycosphaerella fijiensis, Alternaria solani, Aspergillus niger, Cercospora arachidicola, Cladosporium herbarum, Tilletia caries, Tilletia contreversa, Fusarium roseum, Fusarium nivale, Helminthosporium oryzae, Helminthosporium teres, Helminthosporium gramineum, Helminthosporium sativum, Penicillium expansum*, Pestalozzia sp, *Phoma*

*betae, Phoma foveata, Phoma lingam, Ustilago maydis, Ustilago nuda, Ustilago hordei, Ustilago avenae, Verticillium dahliae, Ascochyta pisi, Guignardia bidwellii, Corticium rolfsii, Phomposis viticola, Sclerotinia sclerotiorum, Sclerotinia minor, Coryneum cardinale, Rhizoctonia solani, Acrostalagmus koningi,* Alternaria, Colletotrichum, *Corticium rolfsii, Diplodia natalensis, Gaeumannomyces graminis, Gibberella fujikuroi, Hormodendron cladosporioides, Myrothecium verrucaria, Paecylomyces varioti, Pellicularia sasakii, Phellinus megaloporus, Sclerotium rolfsii, Stachybotris atra, Trichoderma pseudokoningi, Trichothecium roseum.*

The compositions of the invention are especially advantageous on account of their broad spectrum in respect of diseases of cereals (oidia, rust, eyespot, rhynchosporioses, helminthosporioses, septorioses and fusarioses). They are also of great interest on account of their activity against grey mould (Botrytis) and cercosporioses, and as a result they may be applied to multiplication products of crops as varied as vine, market-garden crops and arboriculture, and tropical crops such as groundnut, banana tree, coffee bush, pecan nut and others.

These compositions are also useful in the context of the disinfection of cereal seeds against *Ustilago nuda, Septoria nodorum, Tilletia caries* and *Tilletia controversa,* Helminthosporium, gramineum and many species of the Fusarium sp.

The subject of the invention is also the mixtures of the fungicide a) and one or more fungicides b) and optionally one or more insecticides c) with their preferred variants as have just been described above.

These mixtures are useful in the employment of fungicidal compositions according to the invention.

The subject of the invention is also a method for protecting the multiplication products of plants and the plants resulting therefrom against fungal diseases, wherein the said multiplication products are coated with a fungicidal and non-phytotoxic composition according to the invention.

As stated above, the coating processes are well known in the art, and employ, for seeds, the techniques of film-coating or encapsulation, or for the other multiplication products, the techniques of immersion.

The invention has proved especially advantageous for protecting seeds. Among these seeds, cereal (barley, wheat, rye, oat, triticale), maize and rice seeds may be mentioned.

Preferably, the said seed is coated with 1 to 400 g of fungicide a) and 1 to 400 g of fungicide b) per quintal of seeds.

Nevertheless, within these ranges, those skilled in the art will choose, on the basis of their general body of knowledge and, where appropriate, a few experiments, doses which are non-phytotoxic but effective from a fungicidal standpoint.

Similarly, when the composition contains one or more insecticides, the latter should be applied at non-phytotoxic doses which are well known to those skilled in the art.

Similarly, the subject of the invention is also the multiplication product of plants, coated with a composition according to the invention with the preferred variants stated above.

Preferably, the products are seeds which are advantageously coated with 1 to 400 g of fungicide a) and 1 to 400 g of fungicide b) per quintal of seeds.

The invention is illustrated by the examples given below.

In vivo trial by seed dressing application: Application slurry:

An aqueous dispersion of the active substance mixture to be tested, having the following composition, is prepared by fine grinding:

active substance or active substance mixture (a and/or b),: 60 mg,

Tween 80 (surfactant) consisting of an oleate of a polycondensate of ethylene oxide with a sorbitan derivative, diluted to 10% in water.: 0.3 mg, the mixture is made up to 60 ml with water.

This aqueous dispersion is then diluted with water to obtain the desired concentration.

On *Pythium arrhenomanes:*

Barley seeds, variety Robbin, inoculated artificially with *Pythium arrhenomanes*, are treated with the slurry defined above at the doses shown in the table below.

20 seeds are placed in pots 10 cm×10 cm containing a peat/pozzolana (1:1) mixture.

The plantlets grow and, 15 days after sowing, the state of the latter is observed in comparison with the control, on which colonies of *Pythium arrhenomanes* have grown.

The results below are given for an average of 40 plants (2 pots).

Note: in the subsequent tables, the fungicide a) is designated by the letter a.

|  | dose g/quintal | % efficacy |
|---|---|---|
| maneb | 250 | 38 |
| captan | 160 | 97 |
| thiram | 160 | 100 |
| a + thiram | 100 + 160 | 100 |
| a + captan | 100 + 160 | 90 |
| a + maneb | 100 + 250 | 77 |
| a | 100 | 0 |

No phytotoxic effect is observed.

On *Fusarium culmorum:*

Barley seeds, variety Robbin, naturally contaminated with *Fusarium culmorum* are treated with a slurry defined above at the doses shown in the table below, and planted as described in the above trial.

15 days after sowing, the state of the plantlets is verified in comparison with the untreated control, on which colonies of *Fusarium culmorum* have grown.

The results below are given for an average of forty plants (2 pots).

|  | dose g/quintal | % efficacy |
|---|---|---|
| thiabendazole | 50 | 100 |
| imazalil | 5 | 100 |
| benomyl | 100 | 100 |
| prochloraz | 50 | 100 |
| a + thiabendazole | 25 + 50 | 100 |
| a + imazalil | 25 + 5 | 100 |
| a + prochloraz | 25 + 50 | 100 |
| a | 25 | 100 |

No phytotoxicity is observed.

On *Rhizoctonia solani:*

The trials are performed in the same manner as above, and lead to the results shown in the table below.

|  | dose g/quintal | % efficacy |
|---|---|---|
| flutolanil | 200 | 70 |
| mepronil | 500 | 55 |
| iprodione | 400 | 71 |
| pencycuron | 400 | 55 |

|  | dose g/quintal | % efficacy |
|---|---|---|
| a + flutolanil | 100 + 200 | 82 |
| a + mepronil | 100 + 500 | 73 |
| a + iprodione | 100 + 400 | 70 |
| a + pencycuron | 100 + 400 | 72 |
| a | 100 | 70 |

No phytotoxicity is observed.

On *Pythium arrhenomanes*:

The trials are performed in the same manner as above, and lead to the results shown in the table below.

|  | dose g/quintal | % efficacy |
|---|---|---|
| benalaxyl | 150 | 93 |
| furalaxyl | 150 | 98 |
| etridiazole | 150 | 98 |
| fosetyl-Al | 300 | 80 |
| metalaxyl | 120 | 90 |
| hymexazol | 300 | 37 |
| a + benalaxyl | 100 + 150 | 95 |
| a + furalaxyl | 100 + 150 | 97 |
| a + etridiazole | 100 + 150 | 93 |
| a + fosetyl-Al | 100 + 300 | 80 |
| a + metalaxyl | 100 + 120 | 93 |
| a + hymexazol | 100 + 300 | 32 |
| a | 100 | 0 |

No phytotoxicity is observed.

Combination of phosphite ($K_2PO_4$) and fungicide a:

Barley seeds coated with the slurry defined above are sown in fields on the basis of 120 kg of seeds per hectare.

Reading is performed relative to an untreated control at the time of germination, to which the figure of 100 is assigned.

The biological effect is observed by counting the plants which have emerged, and is expressed in the table below:

| Treatment g/q | % of plants emerged relative to the control |
|---|---|
| control | 100 |
| fungicide a 25 + phosphite 200 | 126 |
| fungicide a 25 + phosphite 40 | 142 |

At 79 days, the plants are uprooted and the number of roots per plant is counted on an average of 20 plants.

| Treatment g/q | Number of roots per plant |
|---|---|
| control | 0.8 |
| fungicide a 25 + phosphite 200 | 5.8 |
| fungicide a 25 + phosphite 40 | 5.5 |

On day 156, the plants are uprooted and the roots are weighed.

| Treatment g/q average of 20 plants | Weight of the roots per plant in mg* |
|---|---|
| control | 74.7 |
| fungicide a 25 + phosphite 200 | 105.5 |
| fungicide a 25 + phosphite 40 | 106 |

*Average of 20 plants

Thus, it is observed that combination promotes rooting, prevents damping-off disease and promotes cereal growth.

We claim:

1. A method for protecting multiplication products of cultivated plants against fungal diseases, comprising coating the multiplication products with a fungicidal and non-phytotoxic amount of a composition comprising a component (a) 2-(4-chlorobenzylidene)-5,5-dimethyl-1-(1H-1,2,4-triazol-1-ylmethyl)-1-cyclopentanol, a component (b) at least one fungicide effective for the protection of multiplication products of cultivated plants selected from the group consisting of iprodione, procymidone and vinclozolin, and an agriculturally acceptable inert vehicle, wherein the weight ratio of component (a) to component (b) is from 1:400 to 400:1.

2. The method according to claim 1, wherein said composition further comprises an insecticidally effective and non-phytotoxic amount of at least one insecticide effective for the protection the multiplication products.

3. The method according to claim 1, wherein said composition further comprises an agriculturally acceptable surfactant.

4. The method according to claim 1, wherein the component (b) fungicide is iprodione.

* * * * *